United States Patent
Taira et al.

(10) Patent No.: US 7,376,368 B2
(45) Date of Patent: May 20, 2008

(54) WATER CONTENT DETERMINATION APPARATUS, IMAGE FORMING APPARATUS, CONTROL METHOD, AND PROGRAM

(75) Inventors: Masayoshi Taira, Kashiwa (JP); Toshifumi Kakutani, Toride (JP); Takashi Sugiura, Kashiwa (JP); Shinichi Takata, Abiko (JP); Yushi Oka, Abiko (JP); Fumitaka Sobue, Toride (JP); Naohisa Nagata, Moriya (JP)

(73) Assignee: Canon Kabushiki Kaisha (JP)

( * ) Notice: Subject to any disclaimer, the term of this patent is extended or adjusted under 35 U.S.C. 154(b) by 146 days.

(21) Appl. No.: 11/364,854

(22) Filed: Feb. 28, 2006

(65) Prior Publication Data

US 2006/0201236 A1    Sep. 14, 2006

(30) Foreign Application Priority Data

Mar. 2, 2005   (JP) .............................. 2005-057749

(51) Int. Cl.
*G03G 21/20* (2006.01)
(52) U.S. Cl. .................... 399/97; 399/44; 324/694; 324/695
(58) Field of Classification Search .................. 399/44, 399/45, 94, 341, 389, 91, 97; 324/694, 695
See application file for complete search history.

(56) References Cited

U.S. PATENT DOCUMENTS

| | | | | |
|---|---|---|---|---|
| 4,356,641 A | * | 11/1982 | Rosenau ....................... 34/537 |
| 4,580,233 A | * | 4/1986 | Parker et al. ................... 73/73 |
| 4,610,530 A | * | 9/1986 | Lehmbeck et al. ........... 399/69 |
| 5,920,751 A | * | 7/1999 | Chow et al. ................... 399/97 |
| 6,125,244 A | * | 9/2000 | Kamiya ........................ 399/44 |
| 7,177,560 B2 | * | 2/2007 | Fujisawa ...................... 399/44 |
| 7,200,345 B2 | * | 4/2007 | Katayanagi et al. .......... 399/45 |
| 2004/0086287 A1 | * | 5/2004 | Minato ......................... 399/44 |
| 2004/0222801 A1 | * | 11/2004 | Becker et al. ............... 324/655 |

FOREIGN PATENT DOCUMENTS

| | | |
|---|---|---|
| JP | 2002-365976 A | 12/2002 |
| JP | 2003-065994 A | 3/2003 |

* cited by examiner

*Primary Examiner*—David M. Gray
*Assistant Examiner*—Kristofferson Service
(74) *Attorney, Agent, or Firm*—Rossi, Kimms & McDowell, LLP

(57) ABSTRACT

An image forming apparatus has a water content determination apparatus that can precisely determining a water content in a medium regardless of an environment where the image forming apparatus is installed. The water content determination apparatus has a detection device that outputs a first signal while the medium is absent in an electrostatic capacitance region formed in a path where the medium is conveyed and outputs a second signal while the medium is present in the electrostatic capacitance region. The temperature in the image forming apparatus is determined based on the first signal. The water content in the medium is determined based on the second signal and the temperature determined by the temperature determination device.

11 Claims, 10 Drawing Sheets

FIG. 3A
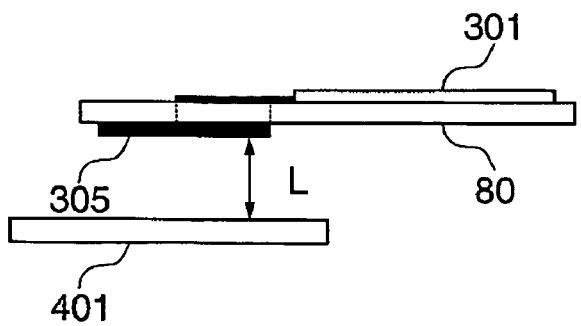
FIG. 3B
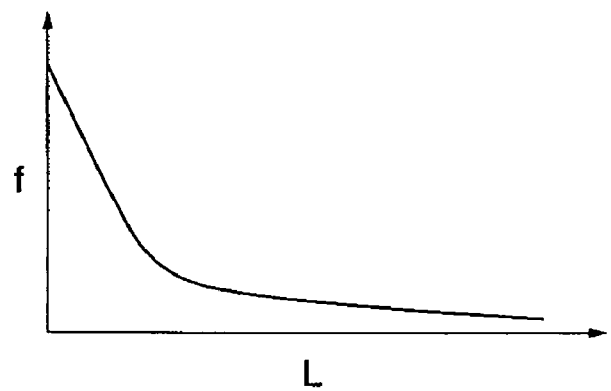
FIG. 3C
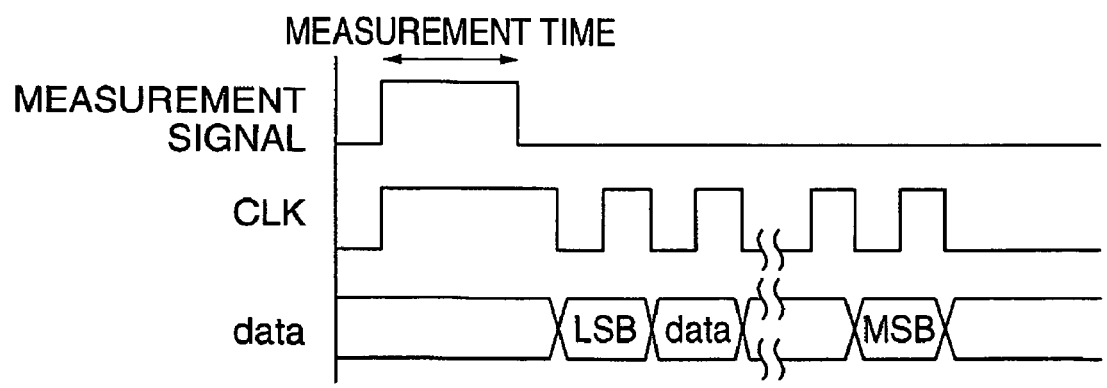
FIG. 3D
| MEASUREMENT TIME | SHORT | ⇔ | LONG |
|---|---|---|---|
| RESOLUTION | ROUGH | ⇔ | FINE |

FIG. 6A

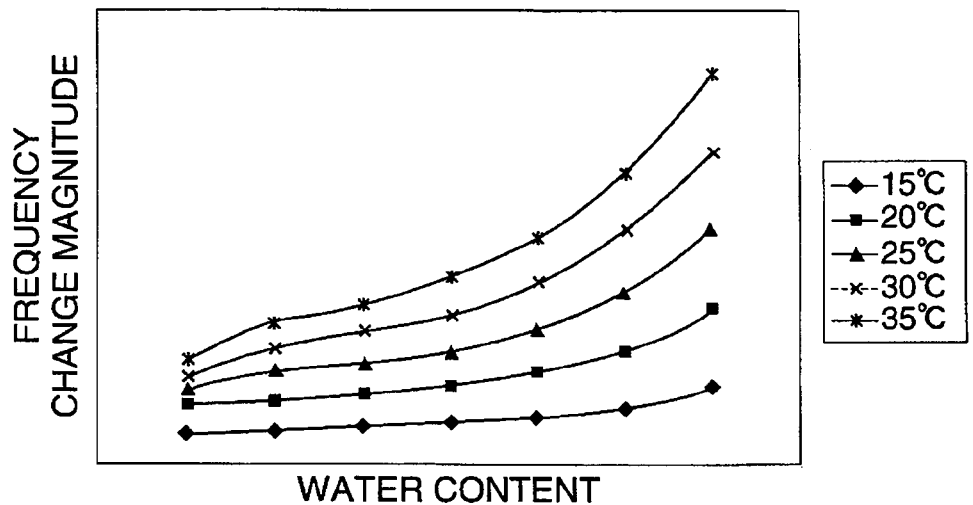

FIG. 6B

| PAPER 1 | | TEMPERATURE [°C] | | | | |
|---|---|---|---|---|---|---|
| | | T1 | T2 | ·· | ·· | Tm |
| FREQUENCY CHANGE MAGNITUDE | f1 | R111[%] | R121[%] | ·· | ·· | ·· |
| | f2 | R112[%] | ·· | ·· | ·· | ·· |
| | : | ·· | ·· | ·· | ·· | ·· |
| | : | ·· | ·· | ·· | ·· | ·· |
| | fn | ·· | ·· | ·· | ·· | R1mn[%] |

FIG. 6C

| PAPER 2 | | TEMPERATURE [°C] | | | | |
|---|---|---|---|---|---|---|
| | | T1 | T2 | ·· | ·· | Tm |
| FREQUENCY CHANGE MAGNITUDE | f1 | R211[%] | R221[%] | ·· | ·· | ·· |
| | f2 | R212[%] | ·· | ·· | ·· | ·· |
| | : | ·· | ·· | ·· | ·· | ·· |
| | : | ·· | ·· | ·· | ·· | ·· |
| | fn | ·· | ·· | ·· | ·· | R2mn[%] |

FIG. 6D

| PAPER X | | TEMPERATURE [°C] | | | | |
|---|---|---|---|---|---|---|
| | | T1 | T2 | ·· | ·· | Tm |
| FREQUENCY CHANGE MAGNITUDE | f1 | Rx11[%] | Rx21[%] | ·· | ·· | ·· |
| | f2 | Rx12[%] | ·· | ·· | ·· | ·· |
| | : | ·· | ·· | ·· | ·· | ·· |
| | : | ·· | ·· | ·· | ·· | ·· |
| | fn | ·· | ·· | ·· | ·· | Rxmn[%] |

| TEMPERATURE | FREQUENCY |
|---|---|
| T1 | f1 |
| T2 | f2 |
| ⋮ | ⋮ |
| ⋮ | ⋮ |
| Tm | fm |

WATER CONTENT DETERMINATION APPARATUS, IMAGE FORMING APPARATUS, CONTROL METHOD, AND PROGRAM

BACKGROUND OF THE INVENTION

1. Field of the Invention

The present invention relates to a water content determination apparatus that determines water content contained in a sheet of paper used for an image forming apparatus such as a copier and a printer, an image forming apparatus, a control method, and a program for implementing the method.

2. Description of the Related Art

Conventionally, an electrophotographic image forming apparatus forms an image by developing a latent image formed on a photosensitive member with toner and transferring a toner image onto a sheet of paper. It is known that as for an electrographic image forming apparatus, the water content contained in a sheet of paper to which toner adheres has some influence on image quality. Some image forming apparatuses of this kind have adopted a method to detect water content contained in a sheet of paper, and then to feed back controlled variable based on the result to the various kinds of controls regarding image forming.

As for a method for detecting water content contained in a sheet of paper, generally, humidity (water content in the air) in the air inside and outside an image forming apparatus is measured with a humidity sensor or the like, and the water content contained in a sheet of paper is relatively estimated based on the measurement value.

However, in the water content estimation method with a humidity sensor, the water content contained in a sheet of paper is not detected directly, but the water content contained in the sheet of paper is estimated based on the measured environment (water content in the air). For example, when a cassette for an image forming apparatus is loaded with sheets of paper brought from another place in a different environment, the sheets of paper neither can absorb the water content that is considered to be contained in the environment, nor let off the water content contained in the sheets of paper. Therefore, a measurement value measured by a humidity sensor measuring the environment in which an image forming apparatus is installed does not always estimate the water content contained in a sheet of paper. Accordingly, it is difficult to obtain data to control an image forming apparatus optimally in the water content estimation method with a humidity sensor.

To solve the above problem, a way of measuring moisture in a sheet of paper directly by measuring the state of the sheet of paper when voltage is applied to it is proposed (refer to Japanese Laid-Open patent publication (Kokai) No. 2002-365976, for example). Furthermore, a way of measuring water content contained in a sheet of paper based on change of electrostatic capacitance while a pair or a plurality of pairs of electrodes are located from across a paper path in such positions as a pair or a plurality of pairs of electrodes sandwich sheets of paper in between (refer to Japanese Laid-Open patent publication (Kokai) No. 2003-065994, for example).

However, in the above conventional water content measurement method with an electrostatic capacitance way, measurement data changes dependent on temperature of the environment where an image forming apparatus is installed. Therefore, there has been a problem that precise water content contained in a sheet of paper cannot be determined because measurement data is different depending on the environment where an image forming apparatus is installed (for example, whether the air-conditioning is kept constant in a room, whether temperature change is great in a room, or whether the place is a cold area or a warm one)

SUMMARY OF THE INVENTION

It is an object of the present invention to provide a water content determination apparatus, an image forming apparatus, and a control method and a program, which are capable of precisely determining water content contained in a medium regardless of an environment where an image forming apparatus is installed.

To attain the above objects, in a first aspect of the present invention, there is provided a water content determination apparatus comprising a detection device that outputs a signal in accordance with presence or absence of a medium in an electrostatic capacitance region formed on a paper path where the medium for image forming is conveyed, a temperature determination device that determines temperature in the water content determination apparatus based on an output signal of the detection device in absence of the medium passing in the electrostatic capacitance region, and a water content determination device that determines water content contained in the medium based on the output signal of the detection device in absence of the medium passing in the electrostatic capacitance region, the output signal of the detection device in presence of the medium passing in the electrostatic capacitance region, and the temperature determined by the temperature determination device.

Preferably, the detection device is provided with a coil, an oscillation device which applies high-frequency voltage to the coil, and a counting device which counts oscillation frequency of the oscillation device, the electrostatic capacitance region is formed on the paper path by generating an electrostatic coupling between a conductor arranged opposite the coil from across the paper path keeping a constant distance and the coil.

Preferably, the temperature determination device determines the temperature referring to a temperature data storing device based on first oscillation frequency data counted by the counting device in absence of the medium passing in the electrostatic capacitance region, the water content determination device determines water content contained in the medium referring to the water content storing device based on the first oscillation frequency data, second oscillation frequency data counted by the counting device in presence of the medium passing in the electrostatic capacitance region, and the temperature determined by the temperature determination device.

Also preferably, the temperature data storing device stores relation of the pre-measured oscillation frequency of the detection device to the temperature, and the water content data storing device stores relation of the pre-measured oscillation frequency of the detection device to the temperature and the water content in respective medium types.

Preferably, the water content determination device further comprises a switching device that switches measurement time for which the detection device operates, wherein the detection device outputs the first oscillation frequency data during the first measurement time switched by the switching device in absence of the medium passing in the electrostatic capacitance region, and outputs the second oscillation frequency data during the second measurement time switched by the switching device in absence of the medium passing in the electrostatic capacitance region.

Also preferably, the second measurement time is set to be equal to or longer than the first measurement time.

Preferably, an image forming apparatus comprises the water content determination device.

Also preferably, controlled variable based on a result of water content determination with the water content determination device is fed back to image forming control.

Also preferably, the image forming apparatus is selected from the group consisting of a printer, a copier, and an MFP.

To attain the above objects, in a second aspect of the present invention, there is provided a water content determination apparatus comprising a detection device that outputs a signal in accordance with presence or absence of a medium in an electrostatic capacitance region formed on a paper path where the medium for image forming is conveyed comprising a temperature determination step that determines temperature in the water content determination apparatus based on an output signal of the detection device in absence of the medium passing in the electrostatic capacitance region, and a water content determination step that determines water content contained in the medium based on the output signal of the detection device in absence of the medium passing in the electrostatic capacitance region, the output signal of the detection device in presence of the medium passing in the electrostatic capacitance region, and the temperature determined by the temperature determination step.

To attain the above objects, in a third aspect of the present invention, there is provided a program for causing a computer to execute a control method of a water content determination apparatus comprising a detection device that outputs a signal in accordance with presence or absence of a medium in an electrostatic capacitance region formed on a paper path where the medium for image forming is conveyed comprising a temperature determination module that determines temperature in the water content determination apparatus based on an output signal of the detection device in absence of the medium passing in the electrostatic capacitance region, and a water content determination module that determines water content contained in the medium based on the output signal of the detection device in absence of the medium passing in the electrostatic capacitance region, the output signal of the detection device in presence of the medium passing in the electrostatic capacitance region, and the temperature determined by the temperature determination module.

BRIEF DESCRIPTION OF THE DRAWINGS

FIGS. 3A to 3D are views which are useful in explaining the operation of the water content detection sensor, FIG. 3A is a view showing the state where the water content detection sensor is located opposite a conductor, FIG. 3B is a view showing the relation of a distance L between a coil unit of the water content detection sensor and a conductor to frequency "f" of voltage which is applied to the coil unit, FIG. 3C is a timing chart showing the measurement signal by a water content detection sensor, a clock for serial communication, and data signal of oscillation frequency, and FIG. 3D is a view showing the relation of measurement time to resolution of a frequency counter;

FIG. 4A is a view showing the construction of a surface of the water content detection sensor on a side where a detection component is located, FIG. 4B is a view showing the construction of a surface of the water content detection sensor on a side where the coil unit is located, and FIG. 4C is a side view showing the construction of the water content detection sensor;

FIG. 5A is a view showing a state where the coil unit of the water content detection sensor is located opposite a paper conveyance guide, FIG. 5B is a view showing the relation of the distance between the coil unit of the water content detection sensor and the paper conveyance guide to the oscillation frequency of the water content detection sensor, and FIG. 5C is a view showing a conceptual circuit diagram comprised of a resonant capacitor, an inductance and an electrostatic capacitance;

FIGS. 6A and 6B are views which are useful in explaining detection of water content contained in a sheet of paper, FIG. 6A is a view showing the relation of oscillation frequency change magnitude of the water content detection sensor to water content, and FIGS. 6B to 6D are views showing water content tables;

FIG. 7A is a view showing the relation of oscillating frequency in an oscillation circuit unit of the water content detection sensor to the temperature, and FIG. 7B is a view showing a temperature table;

DETAILED DESCRIPTION OF THE PREFERRED EMBODIMENTS

The present invention will be described with reference to the drawings showing a preferred embodiment thereof. It should be noted that the relative arrangement of the components, the numerical expressions and numerical values set forth in these embodiments do not limit the scope of the present invention unless it is specifically stated otherwise.

Figure 1:
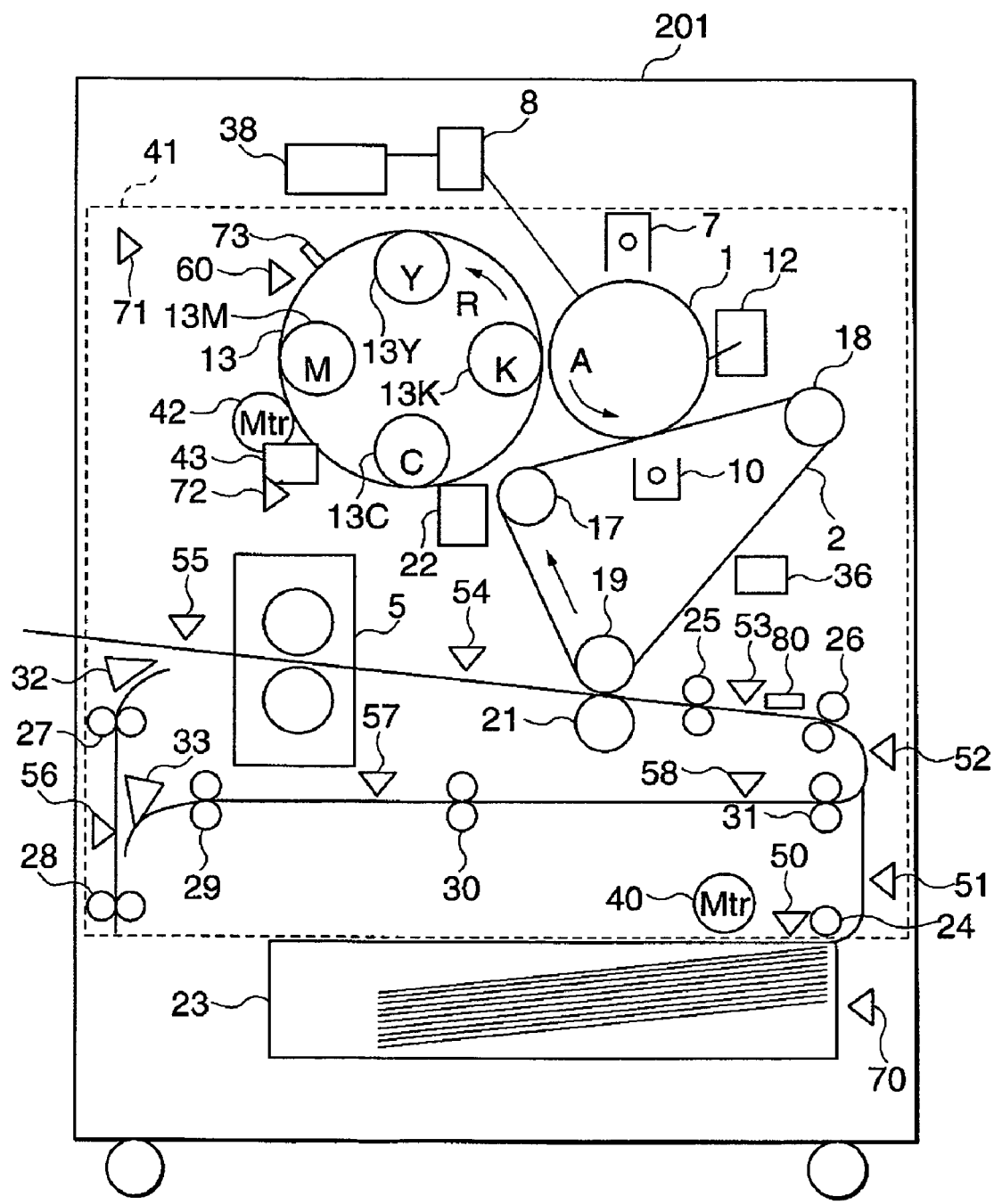
FIG. 1 is a view schematically showing the construction of an image forming apparatus according to an embodiment of the present invention.

FIG. 1 is a view schematically showing the construction of an image forming apparatus according to an embodiment of the present invention.

In FIG. 1, an image forming apparatus 201, for example a full color printer, is provided with a photosensitive drum (hereinafter referred to as a "photoreceptor" for short) 1, an intermediate transfer belt (hereinafter referred to as a "belt" for short) 2, a fixing device 5, a primary charger 7, an exposure device 8, a transfer device 10, a rotating developer 13, a secondary transfer roller 21, a paper cassette 23, and a water content detection sensor 80.

The photoreceptor 1 is an image carrier rotatively driven in the direction of an arrow by a motor (not shown). The belt 2 is worn on a driving roller 17, a tension roller 18, and a backup roller 19. The photoreceptor 1 is surrounded by the primary charger 7, the exposure device 8, the rotating developer 13, the transfer device 10, and a cleaning device 12. The rotating developer 13 houses developing rollers 13Y, 13M, 13C, and 13K for four colors necessary to perform a full color development.

Now the operation of image forming will be explained briefly. After the surface of the photoreceptor 1 is uniformly charged negatively with a predetermined charged part electric potential by the primary charger 7, an image part on the photoreceptor 1 is exposed to the predetermined exposed part electric potential by the exposure device 8, and a latent image corresponding to an image signal generated by an image controller 38 is formed on the photoreceptor 1.

When a latent image on the photoreceptor 1 is developed with respective colors, the rotating developer 13 is rotated in the direction of an arrow R by a driving motor 42, and a position detection flag 73 annexed to the rotating developer 13 is detected with a rotating developer HP sensor 60. Thereby, after a reference position of the rotating developer 13 is detected, the rotating developer 13 is rotated to a predetermined rotation position, and the positioning is performed so that a development roller of a development object color may come into contact with the photoreceptor 1. Development rollers 13Y, 13M, 13C, and 13K to which the developing bias predetermined in respective colors is applied, develop a latent image with toner, and visualize it as a toner image when the photoreceptor 1 passes by a position of each development roller.

After the above development, a toner image on the photoreceptor 1 is transferred onto the belt 2 in a state of being superimposed as a four-color toner image by the transfer device 10. Further, the toner image is transferred onto a sheet of paper by the secondary transfer roller 21, is conveyed to the fixing device 5, and then heat fixed onto the sheet of paper. Lastly, the photoreceptor 1 is ready for next image forming cycle after electricity is removed with a neutralization device (not shown) until voltage becomes almost 0V.

Next, the construction and operation will be explained with the paper conveyance system focused on. A sheet of paper contained in the paper cassette 23 is lifted up to the position where it comes into contact with a pickup roller 24.

A sheet of paper pulled out onto a paper path from a paper cassette 23 by the pickup roller 24 is conveyed to a nip portion (an abutting portion between the secondary transfer roller 21 and the belt 2) by a roller pair 25 and a roller pair 26. A toner image to which the first transfer is performed on the belt 2, the second transfer is performed on one side of the sheet at the nip unit, and heat fixing is performed with the fixing device 5. Then the sheet is discharged out of the device (a discharge unit, not shown).

The water content detection sensor 80 is arranged at a position upstream of the nip portion on the paper path and opposed to a paper conveyance guide (Refer to FIG. 5) from across the paper path. The water content detection sensor 80 is a sensor which is used to determine water content contained in a sheet of paper conveyed on the paper path towards the nip portion with a CPU 901 of the controller 900 which will hereinafter be described with reference to FIG. 2. The construction and operation of the water content detection sensor 80 will hereinafter be described in detail.

When images are formed on double sides of a sheet of paper, respectively, the sheet of paper is conveyed towards a conveyance roller 27 by the movement of a flapper 32 without being discharged out of the device. After the conveyance roller 28 conveys the sheet of paper beyond a flapper 33, it conveys the sheet of paper towards a conveyance roller 29 by reversing the conveyance roller 28 and moving the flapper 33. Furthermore, conveyance rollers 30 and 31 convey the sheet of paper so that it may merge onto the paper path from the paper cassette 23, and have image forming on the other side of the above one side.

Reference numeral 12 denotes a cleaning device that removes residual toner on the photoreceptor 1; 22 a belt cleaner that removes residual toner on the belt 2; 36 a reflective location sensor that detects a reference position; and 43 a solenoid that gets a lock mechanism fixing the position of the rotating developer 13 to operate. Further, reference numeral 50 denotes a paper height sensor that detects height of sheets of paper in the paper cassette 23; 51-58 conveyance sensors that detect presence of sheets of paper or timing of conveying sheets of paper; 70 a cassette insertion sensor that detects insertion of the paper cassette 23; 71 a door opening/closing switch that operates in response to opening or closing of a door 41; and 72 a lock detection sensor that detects operation of the lock mechanism.

Figure 2:
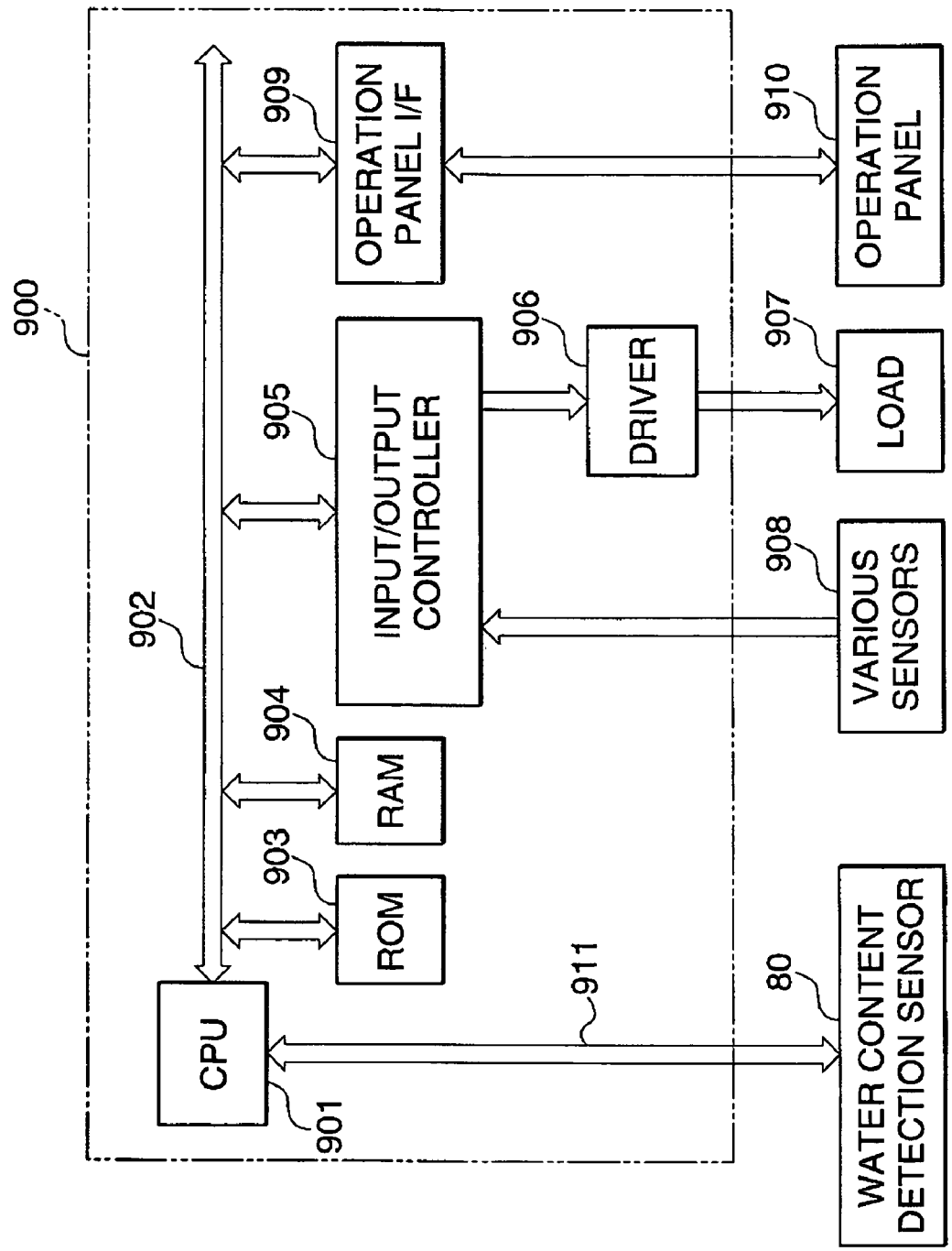
FIG. 2 is a block diagram showing the construction of a water content detection sensor as a water content determination apparatus for an image forming apparatus of FIG. 1, and its controller.

FIG. 2 is a block diagram showing the construction of a water content detection sensor 80 as a water content determination apparatus, and a controller 900 in FIG. 1.

In FIG. 2, the controller 900 in the image forming apparatus 201 is provided with a CPU 901, a bus 902, a ROM 903, a RAM 904, an input/output (I/O) controller 905, a driver 906, an operation panel interface (I/F) 909, and a serial signal line 911.

The controller 900 controls respective units in the image forming apparatus 201. In the controller 900, the CPU 901 is connected to respective units in the controller 900 via the bus 902, and the water content detection sensor 80 via the serial signal line 911. The CPU 901 carries out the procedure of the water content determination process shown in flowcharts in FIGS. 9 and 10. The ROM 903 stores a water content table, a temperature table, and so forth, which will hereinafter be described, as well as the control program. The RAM 904 is used as a temporary storage area for work area of the CPU 901, frequency data, and so forth, which will hereinafter be described.

The input/output controller 905 outputs a control signal to various sensors 908 (the reflective location sensor 30, the rotating developer HP sensor 60, and the lock detection sensor 72 in FIG. 2), inputs detection signals outputted from the various sensors 908, and outputs the control signal to the driver 906. The driver 906 drives loads 907 (the lifter motor 40, the driving motor 42, the solenoid 43, and the other loads), and inputs detection signals outputted from the paper height sensor 50, the conveyance sensors 51-58, the cassette attaching/detaching sensor 70, the door opening/closing switch 71, and the other sensors.

The operation panel interface 909 outputs the control signal to the operation panel 910, and inputs the operation signal outputted from the operation panel 910. The operation panel 910 is provided with a setting unit performing various settings for the image forming apparatus 201, and a display unit displaying set contents and so forth. A user can use the image forming apparatus 201 by inputting various settings such as a desired control mode and a paper type on the operation panel 910. The water content detection sensor 80 detects water content contained in a sheet of paper being conveyed on the paper path, and send/receive signals to/from the CPU 901 via the serial signal line 911.

After the operation of the above water content detection sensor 80 is explained briefly, the water content detection will be described in detail with the water content detection sensor 80.

FIG. 3A is a view showing the state where the water content detection sensor is located opposite a conductor, FIG. 3B is a view showing the relation of distance L between a coil unit and a conductor of the water content detection sensor 80 to frequency "f" of voltage which is applied to the coil unit, FIG. 3C is a timing chart showing the measurement signal by a water content detection sensor, a clock for serial communication, and data signal of oscillation frequency, and FIG. 3D is a view showing the relation of measurement time to resolution of a frequency counter.

Figure 4A:
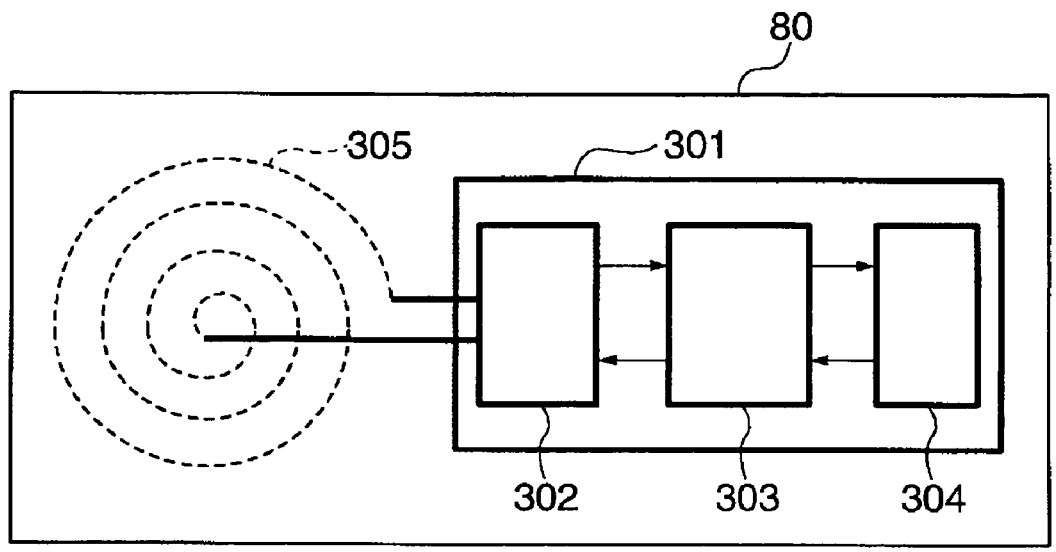
FIGS. 4A to 4C are views schematically showing the construction of the water detection sensor.
Figure 4B:
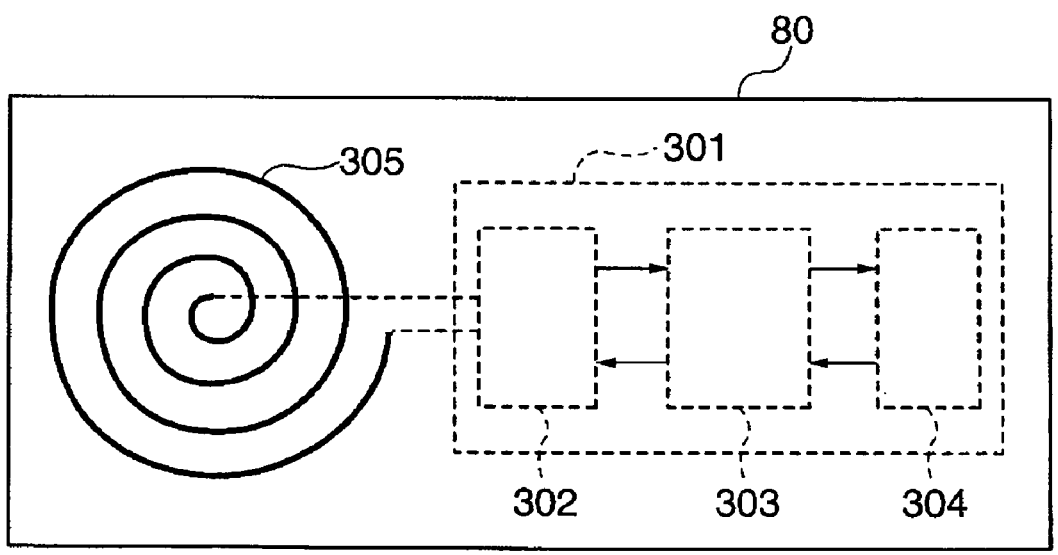
Figure 4C:
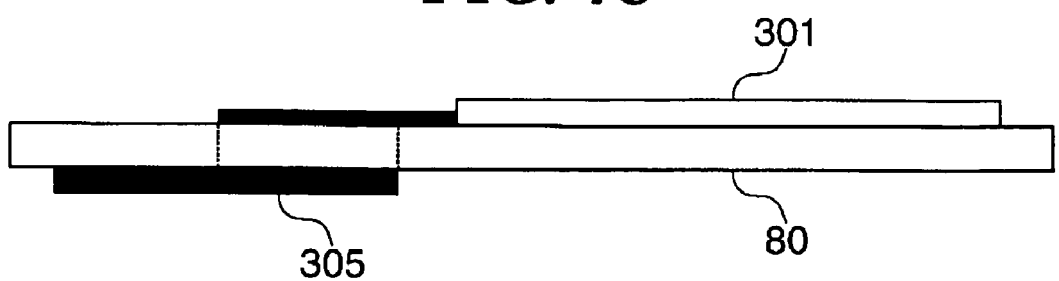

FIG. 4A is a view showing the construction of the water content detection sensor on a side where a detection component is located, FIG. 4B is a view showing the construction of the water content detection sensor on a side where the coil unit is located, and FIG. 4C is a side view showing the construction of the water content detection sensor.

In FIGS. 3A to 3D, as shown in FIG. 3A, if a coil unit 305 to which high-frequency voltage is applied is located opposite a conductor 401 such as metal, electrostatic coupling occurs between the coil unit 305 of the water content detection sensor 80 and the conductor 401. The frequency of the high-frequency voltage which is applied to the coil unit 305 changes according to a distance between the coil unit 305 and the conductor 401, as shown in FIG. 3B.

In FIGS. 4A to 4C, the water content detection sensor 80 is comprised of a board provided with a detection element 301 and the coil unit 305. The detection element 301 is arranged on one side of the board of the water content detection sensor 80 while the coil 305 is arranged on the other side of the board. The coil unit 305 is formed two-dimensionally (planarly), as known from FIG. 4B. In the embodiment of the present invention, explanation will be made using a water content sensor sold on the open market as a water content sensor 80.

The detection element 301 is provided with an oscillation circuit unit 302, a frequency counter 303, and a communication unit 304. The oscillation circuit unit 302 is connected to the coil unit 305, and applies high-frequency voltage to the coil unit 305. The frequency counter 303 counts oscillation frequency in the oscillation circuit unit 302. The communication 304 transmits data on the oscillation frequency counted by the frequency counter 303 to the CPU 901 in the controller 900, and receives data for changing detection precision of the detection element 301 from the CPU 901 based on control signal from the CPU 901.

As shown in FIG. 3C, the signals regarding the water content detection sensor 80 include measurement signal, serial communication clock (hereinafter described as "CLK"), and data signal (hereinafter described as "data") The measurement signal is a signal instructing detection performance outputted to the water content detection sensor 80 via the serial signal line 911. The CLK is a signal outputted to the water content detection sensor 80 via the serial signal line 911. The "data" is a signal indicating the oscillation frequency of the oscillation circuit unit 302 counted by the frequency counter 303 in the water content detection sensor 80.

The water content detection sensor 80 measures signal and outputs the measurement signal only during the measurement time set via the serial signal line 911 by the CPU 901 in the controller 900 when a sheet of paper passes an electrostatic capacitance region (described hereinafter) of a paper path opposite the coil unit 305. After the measurement, the water content detection sensor 80 transmits "data" from LSB (Least Significant Bit) to MSB (Most Significant Bit) to the CPU 901 via the serial signal line 911 in synchronization with the CLK.

Furthermore, as shown in FIG. 3D, the resolution of the frequency counter 303 in the water content detection sensor 80 can be adjusted according to the measurement time set by the measurement signal of the water content detection sensor 80. Namely, when the measurement time is short, the resolution is adjusted roughly, and when the measurement time is long, the resolution is adjusted finely.

Figure 5A:
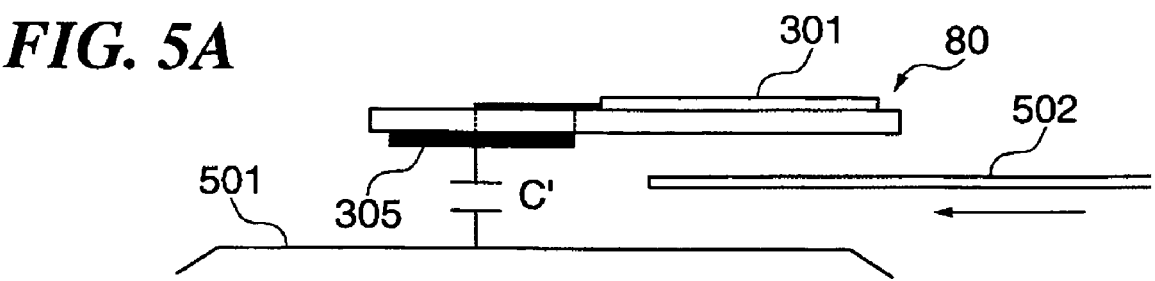
FIGS. 5A to 5C are views which are useful in explaining the output of the water content detection sensor at the time of detecting water content contained in a sheet of paper.
Figure 5B:
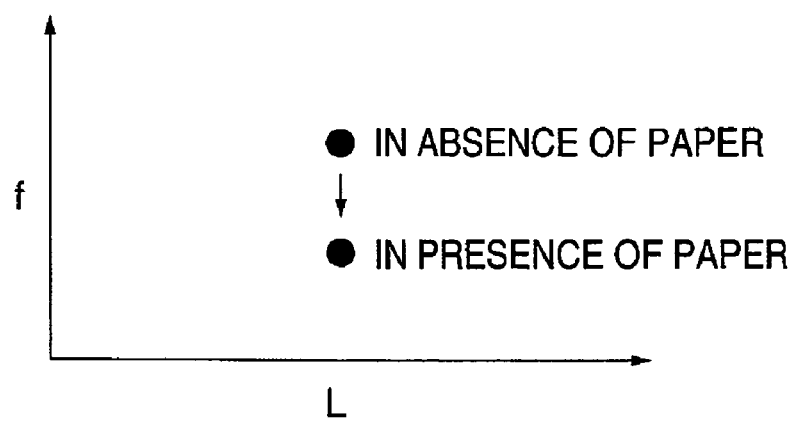
Figure 5C:
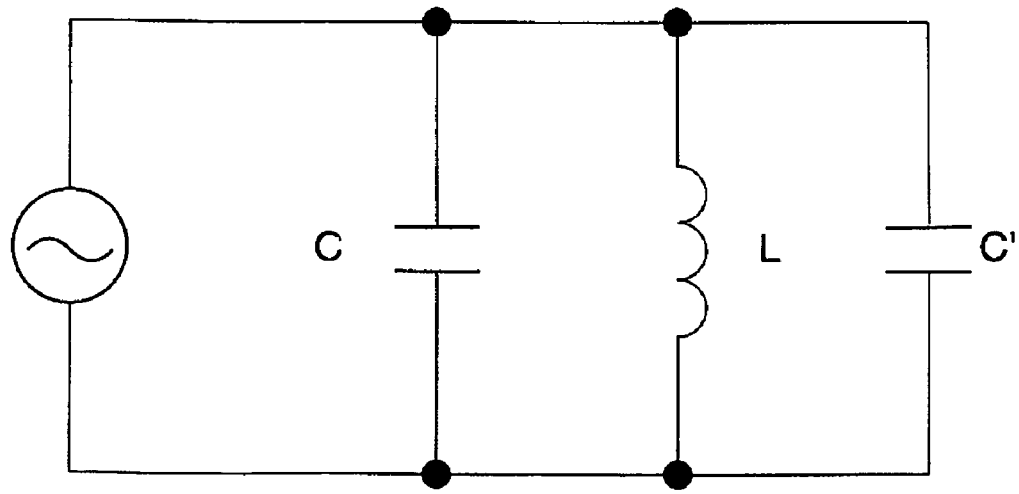

FIG. 5A is a view showing a state where the coil unit 305 of the water content detection sensor 80 is located opposite a paper conveyance guide 501, FIG. 5B is a view showing the relation of distance between the coil unit 305 of the water content detection sensor 80 and the paper conveyance guide 501 to the oscillation frequency of the water content detection sensor 80, and FIG. 5C is a view showing a conceptual circuit diagram comprised of a resonant capacitor, an inductance and an electrostatic capacitance.

In FIG. 5A to 5C, the output of the water content detection sensor 80 at the time of detecting water content contained in a sheet of paper will be explained. As shown in FIG. 5A, the coil unit 305 in the water content detection sensor 80 is located opposite the paper conveyance guide 501 made of metal from across the paper path on which a sheet of paper is conveyed, keeping a constant distance in between.

When a sheet of paper 502 passes the electrostatic capacitance region formed between the coil unit 305 in the water content detection sensor 80 and the opposing paper conveyance guide 501, a dielectric constant of the electrostatic capacitance region increases due to the sheet of paper 502, which decreases the oscillation frequency of the oscillation circuit 302 in the water content detection sensor 80, as shown in FIG. 5B. The method for calculation of the oscillation frequency will be explained hereunder.

If C represents resonant capacitor of the water content detection sensor 80, L represents entire inductance including distribution inductance formed between the coil unit 305 and the paper conveyance guide 501, and C' represents electrostatic capacitance of the electrostatic capacitance region formed between the coil unit 305 and the paper conveyance guide 501, the conceptual circuit diagram is as shown in FIG. 5C. Thereby, the oscillation f can be expressed as the following equation (1).

$$f=1/(2pi*(L*(C+C'))^{1/2}) \quad (1)$$

As known from the above, the sheet of paper 502 passes the electrostatic capacitance region formed between the coil unit 305 of the water content detection sensor 80 and the paper conveyance guide 501, and therefore, the oscillation frequency of the oscillation circuit unit 302 in the water content detection sensor decreases as electrostatic capacitance C' increase.

Next, a manner of detecting of water content contained in a sheet of paper the water content detection sensor 80 uses will be explained.

FIG. 6A is a view showing relation of oscillation frequency change magnitude of the water content detection sensor to water content, and FIGS. 6B to 6D are views showing water content tables.

In FIGS. 6A to 6D, FIG. 6A shows characteristics of oscillation frequency change magnitude of the oscillation circuit unit 302 to water content contained in a sheet of plain paper weighing 209 g/m$^2$, for example, when the sheet of plain paper is present or absent in the electrostatic capacitance region formed between the coil unit 305 of the water content detection sensor 80 and the paper conveyance guide 501. Respective characteristic curves show cases in which temperature in the image forming apparatus 201 is changed (for example, 15° C., 20° C., 25° C., 30° C., and 35° C.), which shows that the frequency change magnitude has water content dependence and temperature characteristic.

As shown in FIGS. 6B to 6D, the CPU 901 in the controller 900 gets the ROM 903 to store the water content table indicating the relation of oscillation frequency change magnitude to the temperature and the water content of the water content detection sensor 80, measured by an experiment the applicant of the present invention made in advance according to the paper type, and refers to the water content table when determining the water content (shown data in the unit of %) contained in a sheet of paper.

Next, a manner of detecting of temperature in the image forming device 201 will be explained.

Figures 7A, 7B:
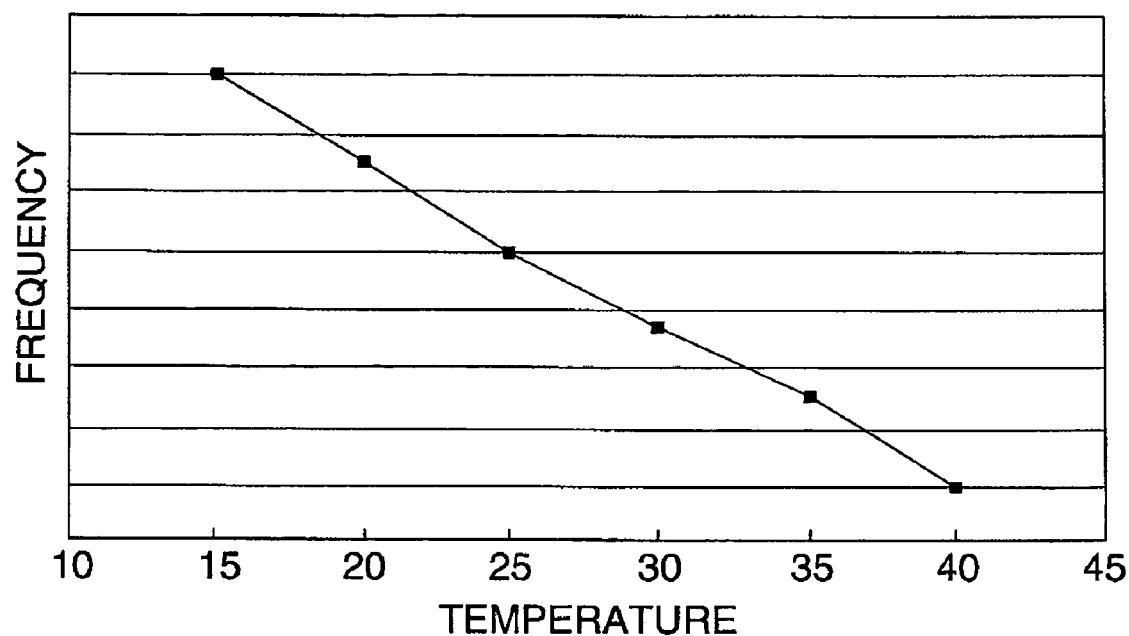
FIGS. 7A and 7B are views explaining detecting temperature in an image forming apparatus.

FIG. 7A is a view showing the relation of oscillating frequency in an oscillation circuit unit of the water content detection sensor to the temperature, and FIG. 7B is a view showing the temperature table.

In FIGS. 7A and 7B, when the coil unit 305 in the water content detection sensor 80 is located opposite the paper conveyance guide 501 keeping a constant distance as shown in FIG. 5A, the oscillation frequency of the oscillation circuit unit 302 in the water content detection sensor 80 changes in response to temperature change in the image forming device 201, as shown in FIG. 7A.

As shown in FIG. 7B, the CPU 901 in the controller 900 gets the ROM 903 to store the water content table indicating the relation of oscillation frequency of the water content detection sensor 80 to the temperature, measured by an experiment the applicant of the present invention made in advance, and refers to the water content table when determining the temperature.

Figure 8:
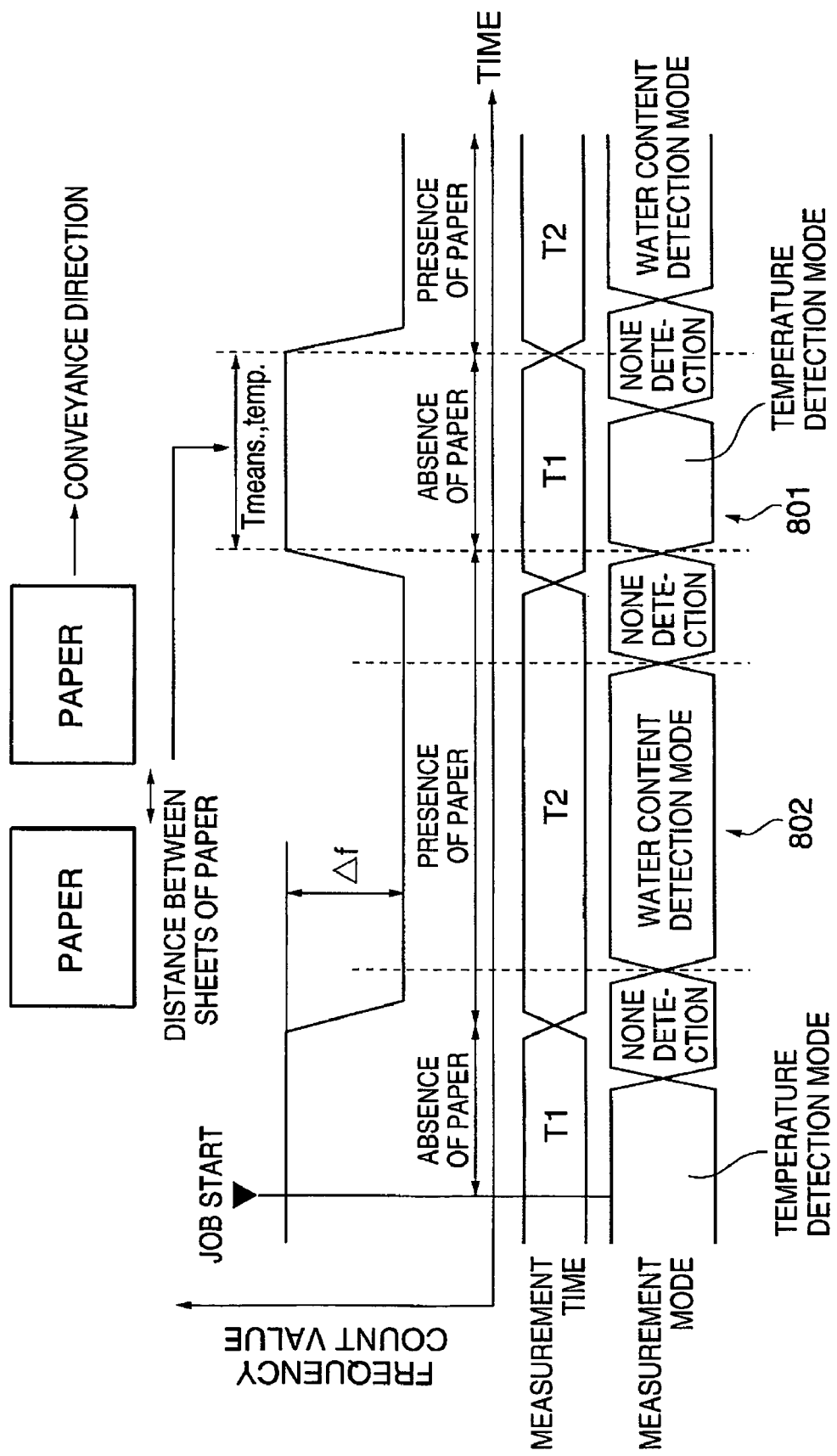
FIG. 8 is a timing chart showing presence or absence of paper on the paper path in the image forming apparatus, measurement time by a water content detection sensor, and the measurement mode.

FIG. 8 is a timing chart showing presence or absence of paper on the paper path in the image forming apparatus 201, measurement time by the water content detection sensor 80, and the measurement mode (a temperature detection mode and a water content detection mode).

In FIG. 8, the water content detection sensor 80 starts working during measurement time T1 when the CPU 901 in the controller 900 detects absence of a sheet of paper by the conveyance sensor 52 arranged upstream of the water content detection sensor 80 after an image forming job is started, namely, when a sheet of paper is absent. Furthermore, the CPU 901 collects data on the oscillation frequency of the oscillation circuit unit 302 from the water content detection sensor 80, and determines temperature in the image forming device 201.

The temperature detection (temperature determination) can be performed during absence of a sheet of paper in the electrostatic capacitance region on the paper path. Therefore, time for the temperature detection mode is Tmeas., temp. (described hereinafter) at a maximum, and the temperature detection is performed during the Tmeas., temp, as shown by a sign 801. Thereafter, the CPU 901 switches the measurement time from T1 to T2 in order to perform water content determination.

Next, the CPU 901 collects data on oscillation frequency of the oscillation circuit unit 302 from the water content detection sensor 80 after based on the output signal of the conveyance sensor 52 the CPU 901 confirms that a sheet of paper has completely moved into the electrostatic capacitance region on the paper path. Furthermore, the CPU 901 determines water content contained in a sheet of paper based on the temperature determined above, the oscillation frequency data in absence of a sheet of paper in the electrostatic capacitance region on the paper path, and the oscillation frequency data in presence of a sheet of paper in the electrostatic capacitance region on the paper path.

The detection of water content (water content determination) contained in a sheet of paper can be performed only during presence of a sheet of paper in the electrostatic capacitance region on the paper path. Therefore, as shown by a sign 802, it is performed in a water content detection mode in which a sheet of paper is present in the electrostatic capacitance region. As shown in FIG. 3D, the measurement time T2 of the water content detection sensor 80 during presence of a sheet of paper in the electrostatic capacitance region is set at as much longer time as possible than the measurement time T1 during absence of a sheet of paper in the electrostatic capacitance region in order to enhance the resolution (T2>T1).

Next, the CPU 901 switches the measurement time to T1 again after the water content determination is finished so that it may perform temperature determination during the time from the time of passage in the electrostatic capacitance region on the paper path of the sheet of paper of which the water content is determined to the time of movement into the electrostatic capacitance region on the paper path of another sheet of paper. Thereafter, the CPU repeats these behaviors, performs the temperature determination and water content determination, and the results of the temperature determination and the water content determination are fed back to the secondary transfer roller 21 located downstream on the paper path of the water content detection sensor 80 for control of the transfer voltage. For example, it can be considered that when water content contained in a sheet of paper is high, transfer voltage is lowered in order to prevent a toner image transferred onto a sheet of paper from blurring.

The measurement time at the time of temperature determination and water content determination is decided dependent on paper conveyance speed in the image forming apparatus 201. In the image forming apparatus 201 in which the paper conveyance speed is V, and the distance between sheets of paper being conveyed continuously is X, the time Tmeas., temp. when the temperature determination can be performed is expressed by the following equation (2);

$$Tmeas., temp. = X/V \qquad (2)$$

Therefore, the time Tmeas., temp. decided by the measurement time T1 at the time of the temperature determination and the equation (2) is expressed by the following equation (3);

$$T1 < Tmeas., temp. \qquad (3)$$

When the time Tmeas., temp. decided by the measurement time T2 at the time of the temperature determination and the equation (2) is expressed by the following equation (4), the measurement time is not required to be switched depending on the time of temperature determination or the time of water content determination, the measurement time T1 and the measurement time T2 can be set at the equal time.

$$T2 < Tmeas., temp. \qquad (4)$$

Namely, if the relation expressed in the equation (4) is true between the measurement time T2 and Tmeas., temp., the equation (3) is always true between the measurement time T1 and Tmeas., temp. Therefore, the measurement time is not required to be switched depending on the time of temperature determination or the time of water content determination.

Next, the water content determination procedure in the image forming apparatus 201 will be explained with reference to the flowcharts in FIGS. 9 and 10.

Figure 9:
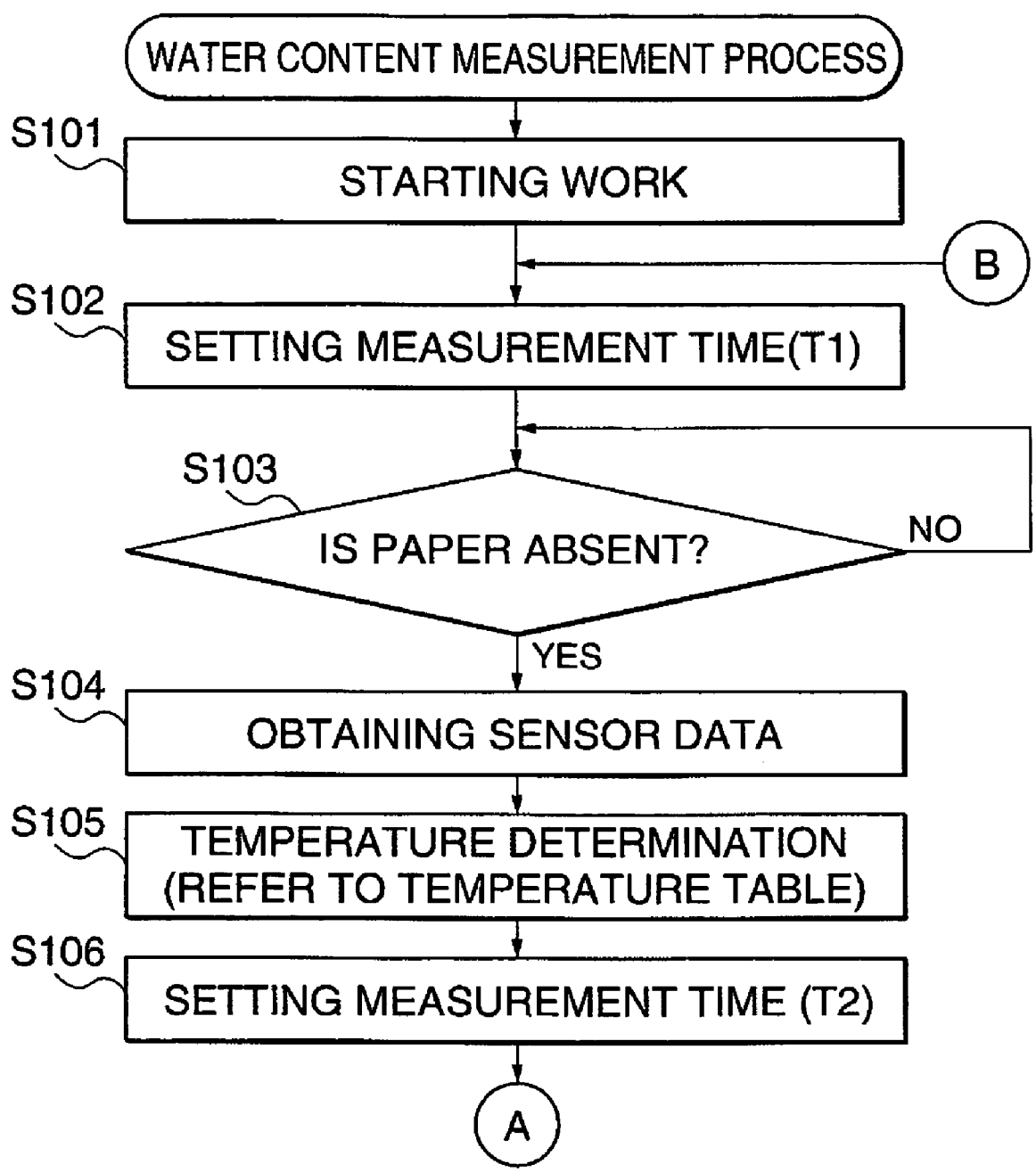
FIG. 9 is a flowchart showing the procedure of water content measurement process that is carried out by the image forming apparatus.
Figure 10:
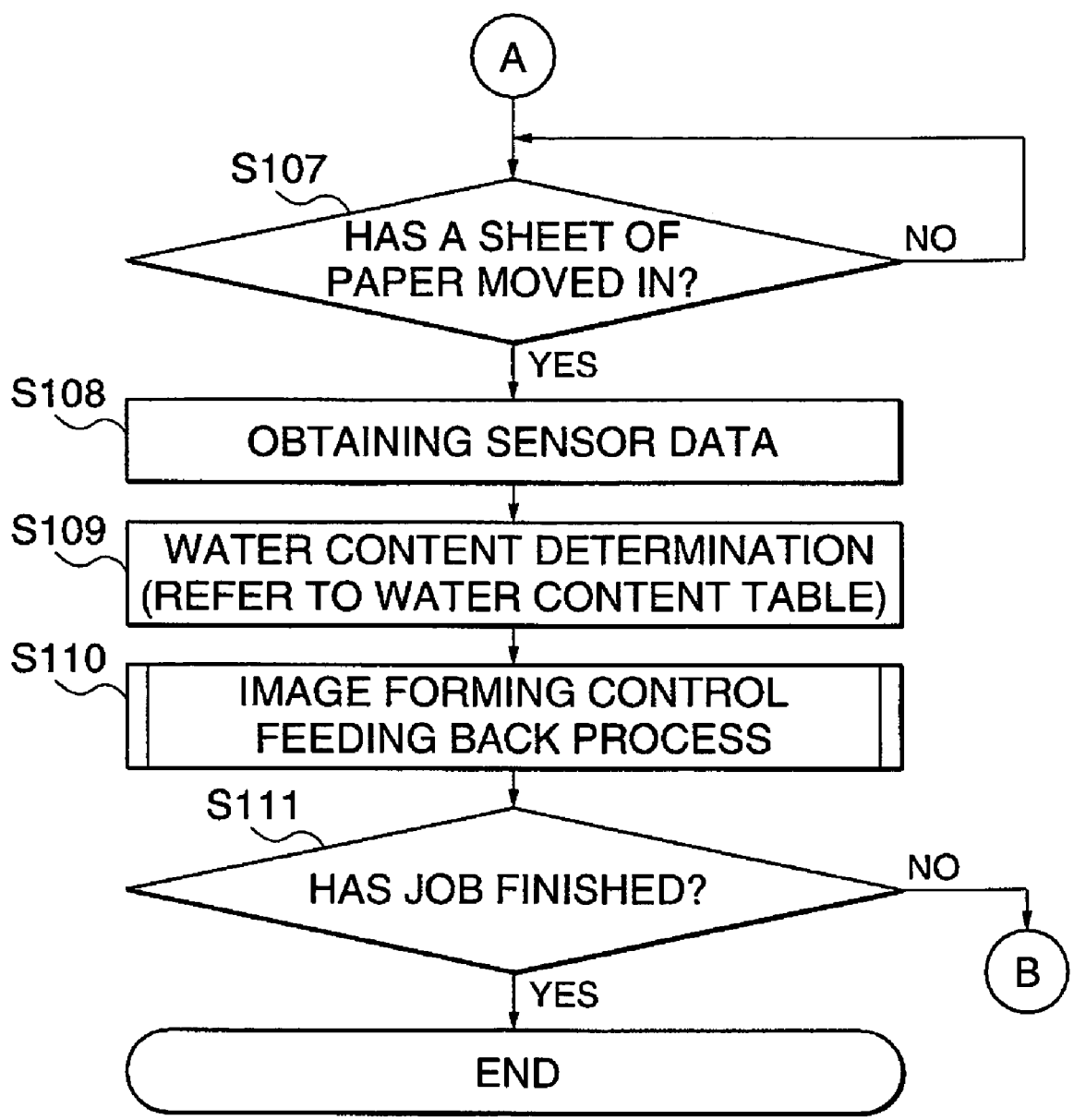
FIG. 10 is a flow chart continued from FIG. 9.

FIGS. 9 and 10 are flowcharts showing the procedure of water content measurement process that is carried out by the image forming apparatus 201.

In FIGS. 9 and 10, first, an operator inputs the paper type for water content measurement from the operation panel 910. The CPU 901 in the controller 900 starts operation of the image forming apparatus 201 (a step S101), and then sets the measurement time T1 at the water content detection sensor 80 via the serial signal line 911 (a step S102).

Next, by the conveyance sensor 52 arranged upstream of the paper path of the water content detection sensor 80, the CPU 901 confirms that a sheet of paper is out of (does not reach) the electrostatic capacitance region on the paper path (YES to a step S103). Furthermore, from the water content detection sensor 80, the CPU 901 obtains the frequency data (in absence of a sheet of paper in the electrostatic capacitance region on the paper path) indicating the oscillation frequency of the oscillation circuit unit 302 counted by the frequency counter 303 in the water content detection sensor 80 to be stored in the RAM 904(a step S104).

Next, referring to the temperature table (FIG. 7B) stored in the ROM 903, the CPU 901 determines the temperature in response to the frequency data obtained in the step S104, and obtains the temperature data in the image forming apparatus 201 (a step S105). After the temperature determination is finished, the CPU 901 set the measurement time T2 at the water content detection sensor 80 via the serial signal line 911 (a step S106).

Next, by the conveyance sensor 52 the CPU 901 confirms that a sheet of paper has completely moved into the electrostatic capacitance region on the paper path (YES to a step S107). Furthermore, from the water content detection sensor 80, the CPU 901 obtains the frequency data (in presence of a sheet of paper in the electrostatic capacitance region on a paper path) indicating the oscillation frequency of the oscillation circuit unit 302 counted by the frequency counter 303 in the water content detection sensor 80 to be stored in the RAM 904 (a step S108).

Next, the CPU 901 searches the water content tables (FIGS. 6B to 6D) for data corresponding to the paper type inputted from the operation panel 910, based on the water content table stored in the ROM 903, based on the frequency data obtained in the step S104 at the time of absence of a sheet of paper (in a state where no sheet of paper is passing) in the electrostatic capacitance region on the paper path, the frequency data obtained in the step S108 at the time of presence of a sheet of paper (in a state where a sheet of paper is passing) in the electrostatic capacitance region on the paper path, and the temperature data determined in the step S105, and determines the water content contained in the sheet of paper (a step S109).

Next, controlled variable corresponding to water content contained in a sheet of paper determined in the step S109 is fed back to image forming control (a step S110). To cite transfer voltage control as image forming control, when water content contained in a sheet of paper is high, the controlled variable is fed back to transfer voltage control of the second transfer roller 21 located downstream of the water content detection sensor 80 on the paper path, and the transfer voltage is lowered in order to prevent a toner image transferred onto a sheet of paper from blurring. Thereafter, the CPU 901 determines whether or not an image forming job is finished (a step S111). If it is not finished, the process returns to the step S102 and repeats the above behaviors, and if it is finished, the process of the image forming apparatus 201 is terminated.

As explained above, according to the present embodiment, in the image forming apparatus 201, water content contained in the sheet of paper is determined, based on the frequency data of the water content detection sensor 80 obtained in absence of a sheet of paper in the electrostatic capacitance region on the paper path, the frequency data of the water content detection sensor 80 obtained in presence of a sheet of paper in the electrostatic capacitance region on the paper path, and temperature in the image forming apparatus 201. Namely, correcting temperature change which has been a problem about water content measurement in the electrostatic capacitance method makes it possible to obtain precise water content contained in a sheet of paper without being influenced by the environment where the image forming apparatus is installed.

Feed back of controlled variable based on the result of the water content determination to image forming control makes it possible to improve image quality.

It is possible to determine temperature in the image forming apparatus 201 without arranging a sensor for temperature measurement anew, thereby reducing the number of parts and the cost.

Other Embodiments of the Present Invention

In the above embodiment of the present invention, in the case of the image forming apparatus 201 as a printer, the control of determining the water content contained in a sheet of paper for the printer is cited as an example. However, the present invention is not limited thereto, but it can be also applied to the control of determining the water content contained in a sheet of paper for a copier, an MFP (Multi-function printer) and so forth.

In the above embodiment of the present invention, there is exemplified a case in which the controlled variable based on the result of the water content determination with the water content detection sensor 80 is fed back to the transfer voltage control, but this invention is not limited thereto. The controlled variable based on the result of the water content determination is fed back to, for example, fixation control, and the control of changing the degree of curling may be performed.

In the above embodiment of the present invention, there is exemplified a case in which the output of the water content detection sensor 80 is used in temperature determination, namely, a case in which the controller 900 performs temperature determination based on the frequency data obtained from the water content sensor 80, but the present invention is not limited thereto. The temperature sensor arranged in the vicinity of the water content detection sensor 80 may directly detect temperature in the image forming apparatus 201.

It goes without saying that the object of the present invention may also be accomplished by supplying a system or an apparatus with a storage medium (or a recording medium) in which a program code of software, which realizes the functions of the above described embodiment is stored, and causing a computer (or CPU or MPU) of the system or apparatus to read out and execute the program code stored in the storage medium.

In this case, the program code itself read from the storage medium realizes the functions of the above described embodiment, and hence the program code and a storage medium on which the program code is stored constitute the present invention.

Further, it is to be understood that the functions of the above described embodiment may be accomplished not only by executing the program code read out by a computer, but also by causing an OS (operating system) or the like which operates on the computer to perform a part or all of the actual operations based on instructions of the program code.

Further, it is to be understood that the functions of the above described embodiment may be accomplished by writing the program code read out from the storage medium into a memory provided in an expansion board inserted into a computer or a memory provided in an expansion unit connected to the computer and then causing a CPU or the like provided in the expansion board or the expansion unit to perform a part or all of the actual operations based on instructions of the program code.

Further, the above program has only to realize the functions of the above-mentioned embodiment on a computer, and the form of the program may be an object code, a program executed by an interpreter, or script data supplied to an OS.

Examples of the storage medium for supplying the program code include a floppy (registered trademark) disk, a hard disk, a magnetic-optical disk, a CD-ROM, a CD-R, a CD-RW, a DVD-ROM, a DVD-RAM, a DVD-RW, a DVD+RW, a magnetic tape, a nonvolatile memory card, and a ROM. Alternatively, the program is supplied by downloading from another computer, a database, or the like, not shown, connected to the Internet, a commercial network, a local area network, or the like.

This application claims priority from Japanese Patent Application No. 2005-057749 filed Mar. 2, 2005, which is hereby incorporated by reference herein in its entirety.

What is claimed is:

1. A water content determination apparatus for determining a water content in a medium conveyed in an image forming apparatus, the water content determining apparatus comprising:
an electrostatic capacitance region positioned in a path where the medium is conveyed in the image forming apparatus;
a detection device that outputs a first signal while the medium is absent in the electrostatic capacitance region and a second signal while the medium is present in the electrostatic capacitance region;
a temperature determination device that determines the temperature in said image forming apparatus based on the first signal output by said detection device while the medium is absent in the electrostatic capacitance region; and
a water content determination device that determines the water content in the medium based on the second signal output by said detection device while the medium is present in the electrostatic capacitance region, and based on the temperature determined by said temperature determination device.

2. A water content determination apparatus as claimed in claim 1, wherein said detection device comprises a coil, an oscillation device which applies high-frequency voltage to said coil, and a counting device which counts oscillation frequency of said oscillation device, said electrostatic capacitance region is formed in said path and provides an electrostatic coupling between a conductor arranged opposite said coil from across said path keeping a constant distance and said coil.

3. A water content determination device as claimed in claim 2, wherein said temperature determination device determines the temperature referring to a temperature table stored in a temperature data storing device based on first oscillation frequency data counted by said counting device while the medium is absent in the electrostatic capacitance region, said water content determination device determines the water content in the medium referring to a water content table stored in a water content storing device based on said first oscillation frequency data, second oscillation frequency data counted by said counting device while the medium is present in the electrostatic capacitance region, and the temperature determined by said temperature determination device.

4. A water content determination device as claimed in claim 3, wherein the temperature table includes relation of the pre-measured oscillation frequency of said detection device to the temperature, and said water content table includes relation of the pre oscillation frequency of said detection device to the temperature and the water content in respective medium types.

5. A water content determination device as claimed in claim 3, further comprising a switching device that switches measurement time for which said detection device operates, wherein said detection device outputs said first oscillation frequency data during a first measurement time switched by said switching device while the medium is absent in the electrostatic capacitance region, and outputs said second oscillation frequency data during a measurement time switched by said switching device while the medium is present in the electrostatic capacitance region.

6. A water content determination device as claimed in claim 5, wherein said second measurement time is set to be equal to or longer than said first measurement time.

7. An image forming apparatus comprising the water content determination device as claimed in claim 1.

8. An image forming apparatus as claimed in claim 7, wherein a controlled variable based on a result of water content determination with said water content determination device is fed back to an image forming control device contained in the image forming apparatus.

9. An image forming apparatus as claimed in claim 7, wherein said image forming apparatus is at least one of a printer, a copier, or an MFP.

10. A method of determining a water content in a medium conveyed in an image forming apparatus, the method comprising:
a step of providing an electrostatic capacitance region positioned in a path where the medium is conveyed in the image forming apparatus;
a step of providing a detection device that outputs a first signal while the medium is absent in the electrostatic capacitance region and a second signal while the medium is present in the electrostatic capacitance region;
a temperature determination step of determining the temperature in said image forming apparatus based on the first signal output by said detection device while the medium is absent in the electrostatic capacitance region; and
a water content determination step of determining the water content in the medium based on the second signal output by said detection device while the medium is present in the electrostatic capacitance region, and based on the temperature determined by said temperature determination step.

11. A computer-readable medium storing a computer program for controlling a water content determination apparatus for determining a water content in a medium conveyed in an image forming apparatus, the water content determination apparatus comprising an electrostatic capacitance region formed in a path where a medium is conveyed in the image forming apparatus, and a detection device that outputs a first signal while the medium is absent in the electrostatic capacitance region and a second signal while the medium is present in the electrostatic capacitance region, the computer program comprising:

a temperature determination module that determines the temperature in said image forming apparatus based on the first signal output by said detection device while the medium is absent in the electrostatic capacitance region; and a water content determination module that determines the water content in the medium based on the second signal output by said detection device while the medium is present in the electrostatic capacitance region, and based on the temperature determined by said temperature determination module.

* * * * *